United States Patent
Egermark et al.

(10) Patent No.: US 10,231,639 B2
(45) Date of Patent: Mar. 19, 2019

(54) ALGORITHM OF NTPROBNP AND HAND HELD ECG TO DETECT ARRHYTHMIA IN AN ELDERLY POPULATION

(71) Applicant: Roche Diagnostics Operations, Inc., Indianapolis, IN (US)

(72) Inventors: Mathias Emil Egermark, Muri bei Bern (CH); Edelgard Anna Kaiser, Huenenberg See (CH); Ursula-Henrike Wienhues-Thelen, Krailling (DE); Christian Zaugg, Rheinfelden (CH); Andre Ziegler, Laeufelfingen (CH); Marten Rosenquist, Stockholm (SE); Viveka Frykmann-Kull, Vaxholm (SE); Emma Svennberg, Djursholm (SE); Leif Friberg, Bromma (SE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 15/132,318

(22) Filed: Apr. 19, 2016

(65) Prior Publication Data
US 2017/0296078 A1    Oct. 19, 2017

(51) Int. Cl.
*A61B 5/04*    (2006.01)
*A61B 5/046*    (2006.01)
(Continued)

(52) U.S. Cl.
CPC ............ *A61B 5/046* (2013.01); *A61B 5/0404* (2013.01); *A61B 5/04085* (2013.01);
(Continued)

(58) Field of Classification Search
CPC ... A61N 1/046; A61N 1/0404; A61N 1/04085
See application file for complete search history.

(56) References Cited

U.S. PATENT DOCUMENTS

| 4,016,043 A | 4/1977 | Schuurs et al. |
| 4,018,653 A | 4/1977 | Mennen |

(Continued)

FOREIGN PATENT DOCUMENTS

| WO | 2012/107419 A1 | 8/2012 |
| WO | 2014/072500 A1 | 5/2014 |

OTHER PUBLICATIONS

Alonso, Alvaro et al., Chronic Kidney Disease is Associated with the Incidence of Atrial Fibrillation: the Atherosclerosis Risk in Communities (ARIC) Study, Circulation, 2011, pp. 2946-2953, vol. 123, No. 25.

(Continued)

*Primary Examiner* — Mallika D Fairchild
(74) *Attorney, Agent, or Firm* — Roche Diagnostics Operations, Inc.

(57) ABSTRACT

The present invention relates to a method of diagnosing whether a subject with no known history of atrial fibrillation is suffering from atrial fibrillation, or not, said method comprising the steps of a) determining the amount of a BNP-type peptide in a sample of said subject; b) comparing the amount the BNP-type peptide to a reference, and c) assessing intermittent ECG recordings obtained from said subject over a period of at least one week by using a handheld ECG device.

14 Claims, 4 Drawing Sheets

(51) Int. Cl.
    A61B 5/0404    (2006.01)
    A61B 5/0408    (2006.01)
    G01N 33/74     (2006.01)
(52) U.S. Cl.
    CPC ...... *G01N 33/74* (2013.01); *A61B 2560/0468* (2013.01); *G01N 2800/326* (2013.01)

(56) References Cited

U.S. PATENT DOCUMENTS

| | | | |
|---|---|---|---|
| 4,424,279 A | 1/1984 | Bohn et al. | |
| 8,506,499 B2* | 8/2013 | Mukherjee | G01N 33/6893 600/508 |
| 2006/0155200 A1* | 7/2006 | Ng | A61B 5/0472 600/509 |
| 2009/0054741 A1* | 2/2009 | McAleer | A61B 5/0205 600/301 |
| 2014/0206976 A1* | 7/2014 | Thompson | A61B 5/0006 600/391 |

OTHER PUBLICATIONS

Alonso, Alvaro et al., Simple Risk Model Predicts Incidence of Atrial Fibrillation in a Racially and Geographically Diverse Population: the CHARGE-AF Consortium, Journal of the American Heart Association, 2013, 11 pps., vol. 2, e000102.

Aronsson, Mattias et al., The cost-effectiveness of radiofrequency catheter ablation as first-line treatment for paroxysmal atrial fibrillation: results from a MANTRA-PAF substudy, Europace, 2015, pp. 48-55, vol. 17.

Bertsch, Thomas et al., Multicentre Analytical Evaluation of an New Point-Of-Care System for the Determination of Cardiac and Thromboembolic Markers, Clinical Laboratory, 2010, pp. 37-49, vol. 56.

Camm, A. John et al., 2012 focused update of the ESC Guidelines for the management of atrial fibrillation, European Heart Journal, 2012, pp. 2719-2747, vol. 33.

Camm, A. John et al., The Task Force for the Management of Atrial Fibrillation of the European Society of Cardiology (ESC), European Heart Journal, 2010, pp. 2369-2429, vol. 31.

Camm, A. John et al., Usefulness of Continuous Electrocardiographic Monitoring for Atrial Fibrillation, American Journal of Cardiology, 2012, pp. 270-276, vol. 110.

Das, Sandeep R. et al., Impact of Body Mass and Body Composition on Circulating Levels of Natriuretic Peptides, Circulation, 2005, pp. 2163-2168, vol. 112.

Doliwa, Peter Sobocinski et al., Short-term ECG for out of hospital detection of silent atrial fibrillation episodes, Scandinavian Cardiovascular Journal, 2009, pp. 163-168, vol. 43.

Doliwa, Piotr Sobocinski et al., Paroxysmal atrial fibrillation with silent episodes: Intermittent versus continuous monitoring, Scandinavian Cardiovascular Journal, 2012, pp. 144-148, vol. 46.

Fitzmaurice, David A. et al., Screening versus routine practice in detection of atrial fibrillation in patients aged 65 or over: cluster randomized controlled trial, BMJ Online First, 2007, 6 pps.

Flaker, Greg C. et al., Asymptomatic atrial fibrillation: Demographic features and prognostic information from the Atrial Fibrillation Follow-up Investigation of Rhythm Management (AFFIRM) study, American Heart Journal, 2005, 657-663, vol. 149, No. 4.

Folsom, Aaron R. et al., Troponin T, NT-pro BNP, and Incidence of Stroke: The Atherosclerosis Risk in Communities (ARIC) Study, Stroke, 2013, pp. 961-967, vol. 44, No. 4.

Fradley, Michael G. et al., Reference Limits for N-terminal-pro-B-type Natriuretic Peptide in Healthy Individuals (From the Framingham Heart Study), American Journal of Cardiology, 2011, pp. 1341-1345, vol. 108, No. 9.

Friberg, Leif et al., Increased mortality in paroxysmal atrial fibrillation: report from the Stockholm Cohort-Study of Atrial Fibrillation (SCAF), European Heart Journal, 2007, pp. 2346-2353, vol. 28.

Friberg, Leif et al., Population screening of 75- and 76-year-old men and women for silent atrial fibrillation (STROKESTOP), Europace, 2013, pp. 135-140, vol. 15.

Fuster, Valentin et al., ACC/AHA/ESC 2006 Guidelines for the Management of Patients With Atrial Fibrillation, Circulation, 2006, pp. e257-e354, vol. 114, No. 7.

Go, Alan S. et al., Prevalence of Diagnosed Atrial Fibrillation in Adults, JAMA, 2001, pp. 2370-2375, vol. 285.

Hart, Robert G. et al., Meta-analysis: Antithrombotic Therapy to Prevent Stroke in Patients Who Have Nonvalvular Atrial Fibrillation, Annals of Internal Medicine, 2007, pp. 857-867, vol. 146.

Healey, Jeff S. et al., Subclinical Atrial Fibrillation and the Risk of Stroke, The New England Journal of Medicine, 2012, pp. 120-129, vol. 366.

Hijazi, Ziad et al., Biomarkers in atrial fibrillation: a clinical review, European Heart Journal, 2013, pp. 1475-1480, vol. 34.

Hijazi, Ziad et al., Cardiac Biomarkers Are Associated With an Increased Risk of Stroke and Death in Patients With Atrial Fibrillation, Circulation, 2012, pp. 1605-1616, vol. 125.

Hijazi, Ziad et al., N-Terminal Pro-B-Type Natriuretic Peptide for Risk Assessment in Patients With Atrial Fibrillation, Journal of the American College of Cardiology, 2013, pp. 2274-2284, vol. 61, No. 22.

Hunt, Sharon A. et al., ACC/AHA Guidelines for the Evaluation and Management of Chronic Heart Failure in the Adult: Executive Summary, Journal of the American College of Cardiology, 2001, pp. 2101-2113, vol. 38, No. 7.

Hunt, Sharon Ann et al., ACC/AHA 2005 Guideline Update for the Diagnosis and Management of Chronic Heart Failure in the Adult, Journal of the American College of Cardiology, 2005, pp. e1-e82, vol. 46.

Llombart, Victor et al., B-Type Natriuretic Peptides Help in Cardioembolic Stroke Diagnosis Pooled Data Meta-Analysis, Stroke, 2015, pp. 1187-1195, vol. 46.

Lowres, Nicole et al., Screening to identify unknown atrial fibrillation A systematic review, Thrombosis and Haemostasis, 2013, pp. 213-222, vol. 110.

Madamanchi, Chaitanya et al., Obesity and Natriuretic Peptides, BNP and NT-proBNP: Mechanisms and Diagnostic Implications for Heart Failure, International Journal of Cardiology, 2014, pp. 611-617, vol. 176, No. 63.

Mozaffarian, Dariush et al., Heart Disease and Stroke Statistics— 2016 Update, Circulation, 2015, pp. e38-e360, vol. 133.

Okada, Y. et al., Brain natriuretic peptide as a predictor of delayed atrial fibrillation after ischaemic stroke and transient ischaemic attack, European Journal of Neurology, 2010, pp. 326-331, vol. 17.

Orrsjö, Gustav et al., Screening of Paroxysmal Atrial Fibrillation after Ischemic Stroke: 48-Hour Holter Monitoring versus Prolonged Intermittent ECG Recording, ISRN Stroke, 2014, 6 pps., Hindwai Publishing Corporation.

Patton, Kristen K. et al., N-terminal pro-B-type natriuretic peptide as a predictor of incident atrial fibrillation in the Multi-Ethnic Study of Atherosclerosis: the effects of age, sex and ethnicity, Heart, 2013, pp. 1832-1836, vol. 99.

Patton, Kristen K. et al., N-terminal pro-B-type Natriuretic Peptide is a Major Predictor of the Development of Atrial Fibrillation: The Cardiovascular Health Study, Circulation, 2009, pp. 1768-1774, vol. 120, No. 18.

Redfield, Margaret M. et al., Plasma Brain Natriuretic Peptide Concentration: Impact of Age and Gender, Journal of the American College of Cardiology, 2002, pp. 976-982, vol. 40, No. 5.

Richter, Mark M., Electrochemiluminescence (ECL), Chemical Reviews, 2004, pp. 3003-3036, vol. 104.

Rivera, Miguel et al., Obese subjects with heart failure have lower N-terminal pro-brain natriuretic peptide plasma levels irrespective of aetiology, The European Journal of Heart Failure, 2005, pp. 1168-1170, vol. 7.

Schnabel, Renate B. et al., Development of a Risk Score for Atrial Fibrillation in the Community The Framingham Heart Study, Lancet, 2009, pp. 739-745, vol. 373, No. 9665.

Schnabel, Renate B. et al., Relations of Biomarkers of Distinct Pathophysiological Pathways and Atrial Fibrillation Incidence in the Community, Circulation, 2010, pp. 200-207, vol. 121, No. 2.

(56) References Cited

OTHER PUBLICATIONS

Seegers, Joachim et al., Natriuretic peptides for the detection of paroxysmal atrial fibrillation, Open Heart, 2015, e000182, 6 pps., vol. 2.

Sobocinski, Piotr Doliwa et al., Improved screening for silent atrial fibrillation after ischaemic stroke, Europace, 2012, pp. 1112-1116, vol. 14.

Svennberg, Emma et al., Mass Screening for Untreated Atrial Fibrillation The STROKESTOP Study, Circulation, 2015, pp. 2176-2184, vol. 131.

Svennberg, Emma et al., NT-proBNP and silent atrial fibrillation—The STROKESTOP II study, Presentation at 10th International Biomarker Workshop, Apr. 26, 2015, 37 pages.

Wachter, Rolf et al., Natriuretic Peptides for the Detection of Paroxysmal Atrial Fibrillation in Patients with Cerebral Ischemia—The Find-AF Study, PLoS One, 2012, e34351, 7 pps., vol. 7, Issue 4.

Wang, Angela Yee-Moon, Clinical Utility of Natriuretic Peptides in Dialysis Patients, Seminars in Dialysis, 2012, pp. 326-333, vol. 25, No. 3.

Wang, Thomas J. et al., Obesity and the Risk of New-Onset Atrial Fibrillation, Journal of the American Medical Association, 2004, pp. 2471-2477, vol. 292, No. 20.

Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.

\* cited by examiner

Flowchart: Method of diagnosing whether a subject with no known history of atrial fibrillation is suffering from atrial fibrillation

ALGORITHM OF NTPROBNP AND HAND HELD ECG TO DETECT ARRHYTHMIA IN AN ELDERLY POPULATION

BACKGROUND

The present invention relates to a method of diagnosing whether a subject with no known history of atrial fibrillation is suffering from atrial fibrillation or not, said method comprising the steps of a) determining the amount of a BNP-type peptide in a sample of said subject; b) comparing the amount of the BNP-type peptide to a reference, and c) assessing intermittent ECG recordings obtained from said subject over a period of at least one week by using a handheld ECG device.

Atrial fibrillation (AF) is the most common type of heart arrhythmia and one of the most widespread conditions among the population. AF is characterized by irregular heart beating and often starts with brief periods of abnormal beating that can increase over time and may become a permanent condition. An estimated 2.7-6.1 million people in the United States have AF. However, many more people are likely to be affected by the condition because atrial fibrillation often comes and goes and does not always cause symptoms (Camm et al., Am J Cardiol. 2012; 110:270-6). Around a third of all atrial fibrillation patients have no symptoms and are therefore rarely discovered in routine health checks (Mozaffarian et al., Circulation. 2016; 133: e38-e360).

The diagnosis of heart arrhythmia such as atrial fibrillation typically involves determination of the cause of the arrhythmia, and classification of the arrhythmia. Guidelines for the classification of atrial fibrillation according to the American College of Cardiology (ACC), the American Heart Association (AHA), and the European Society of Cardiology (ESC) are mainly based on simplicity and clinical relevance. The first category is called "first detected AF". People in this category are initially diagnosed with AF and may or may not have had previous undetected episodes. If a first detected episode stops on its own in less than one week, but is followed by another episode later on, the category changes to "paroxysmal AF". Although patients in this category have episodes lasting up to 7 days, in most cases of paroxysmal AF the episodes will stop in less than 24 hours. If the episode lasts for more than one week, it is classified as "persistent AF". If such an episode cannot be stopped, i.e. by electrical or pharmacologic cardioversion, and continues for more than one year, the classification is changed to "permanent AF". However, episodes that last less than 30 seconds are not considered in this classification system and often remain undetected in routine health checks. The correct and early diagnosis of atrial fibrillation can thus be challenging.

The recording of the electrical activity of the heart over a period of time called electrocardiography (ECG) is essential for specific detection of heart arrhythmia and diagnosis of atrial fibrillation. However, the difficulty of diagnosing atrial fibrillation using ECG lies in the fact that the arrhythmias may occur at long intervals. Further potential symptoms such as dizziness, fainting, shortness of breath and heart palpitations may arise in a few seconds but are unspecific and disappear just as quickly, which is why they are difficult to detect with a regular resting ECG at a hospital or with a continuous ECG over a few days. The likelihood of discovering arrhythmia increases significantly when the length of the investigation can be extended and the readings are taken continuously and/or repeatedly. Handheld ECG devices allow patients to register their ECG data themselves and may be prescribed to a patient for better arrhythmia detection and management. Most of the handheld devices have simple metal contacts that the user can place their thumbs or other fingers on or place against bare skin, such as on the chest. These devices are more convenient and faster to use than the usual adhesive skin electrodes. An example of such a Handheld ECG device is the one-lead ECG recorder from Zenicor. Using this device, patients can record ECG readings by placing their thumbs on two electrodes for 30 seconds. Multiple ECG readings of 10-30 seconds may be stored or transferred to a central ECG database via a built-in mobile phone.

The device has been shown to have higher sensitivity for detection of AF than conventional 24-hour Holter recordings and has been used in a mass screening study for atrial fibrillation (Svennberg et al., Circulation 2015, Vol. 131, p. 2176-84).

An early diagnosis of atrial fibrillation is highly desired because atrial fibrillation is an important risk factor for stroke and systemic embolism (Hart et al., Ann Intern Med 2007; 146(12): 857-67; Go A S et al. JAMA 2001; 285(18): 2370-5). The most feared consequence of atrial fibrillation is (ischemic) stroke, which occurs when blood flow to the brain is blocked by a clot or by fatty deposits called plaque in the blood vessel lining. Regardless of symptomatology, the individuals with atrial fibrillation have a 5-fold increased risk of ischemic stroke (Healey et al., N Engl J Med. 2012; 366:120-9; Flaker et al., Am Heart J. 2005; 149:657-63; Friberg et al., Eur Heart J. 2007; 28:2346-53). Moreover, strokes caused by complications from AF tend to be more severe than strokes with other underlying causes. Stroke caused by atrial fibrillation gives rise to more debilitating disabilities and has a higher mortality rate. At least 30% of all stroke patients are estimated to have atrial fibrillation, so that oral anticoagulation (OAC) for stroke prevention has become a beneficial, common treatment.

Assessment of atrial fibrillation-associated stroke risk is at present mainly based on clinical risk scores such as CHADS2 and CHA2DS2-VASc (Camm et al., Eur Heart J. 2012; 33:2719-47). However, these scores provide only modest discrimination of risk for individual patients. Several biomarkers have been suggested to refine the risk assessment in atrial fibrillation for stroke outcomes and for mortality such as the cardiac biomarkers troponin and natriuretic peptides, markers of renal function, coagulation, and inflammation (Hijazi et al., Eur Heart J. 2013 May; 34(20):1475-80). The natriuretic peptides N-terminal pro brain-type natriuretic peptide (NT-proBNP), brain-type natriuretic peptide (BNP) and N-terminal pro atrial-type natriuretic peptide (NT-proANP) have been reported to be useful for the detection of paroxysmal atrial fibrillation in patients with cerebral ischemia (Wachter et al., PLOS one 2012; 7: e34351).

A stroke is often a disaster for those affected. A third of all those who have had a stroke die, and a further third are severely disabled for life. In addition, stroke is one of the diseases that results in the highest medical costs. The estimated direct medical cost of stroke in 2011 to 2012 (average annual) was $33.0 billion (MEPS, NHLBI tabulation). Between 2012 and 2030, total direct medical stroke-related costs are projected to triple, from $71.6 billion to $184.1 billion, with the majority of the projected increase in costs arising from those 65 to 79 years of age (Mozaffarian et al., Circulation. 2016; 133:e38-e360). Many of these cases can be prevented if atrial fibrillation is diagnosed and treated at an early stage. The most important treatment for stroke prevention in atrial fibrillation is anticoagulant medication, which strongly reduces the risk of stroke. People older than 75 years have a 25% risk for stroke during a five-year period. Anticoagulation treatment can prevent about 70% of strokes, if it is prescribed. In recent years new anticoagulants have been launched on the market as an alternative to traditional vitamin K antagonist treatment. Stroke prevention in cases of atrial fibrillation and primary population screening to identify individuals with low risk for stroke have been highlighted as an issue of priority. Early identification of AF could be beneficial as a stroke-preventive measure, since initiation of protective OAC treatment can be made. Opportunistic screening for AF using pulse-palpation is now recommended above age 65 according to the latest European Society of Cardiology's guidelines (Fitzmaurice et al., Bmj. 2007; 335:383), and has a detection rate of new AF of 1.6% (Lowres et al., Thromb Haemost. 2013; 110:213-22).

Screening for AF using "one-off" 12-lead ECG has in a meta-analysis identified new AF in 1.4% of >65 year olds (Lowres et al., Thromb Haemost. 2013; 110:213-22). In the systematic screening study STROKESTOP, a total of 7,173 individuals aged 75/76 years in two Swedish regions were prospectively screened for silent AF using intermittent ECG recordings for two weeks. This yielded 3% individuals with newly detected AF (NDAF), and increased the AF prevalence by more than 30% (Svennberg et al., Circulation. 2015: Vol. 131, p. 2176-84).

N-terminal prohormone of brain natriuretic peptide (NT-proBNP) is an established biomarker, clinically used mainly as a biomarker of cardiac dysfunction and fluid overload in congestive heart failure. More recently NT-proBNP has in several large cohort studies emerged as an independent predictor for incipient AF (Folsom et al., Stroke. 2013; 44:961-7; Patton et al., Circulation. 2009; 120:1768-1774; Patton et al., Heart. 2013; 99:1832-6; Schnabel et al., Circulation. 2010; 121:200-7; Okada et al., Eur J Neurol. 2010; 17:326-31; Seegers et al., Open Heart. 2015; 2:e000182).

In addition patients with AF and a high level of NT-proBNP have a higher risk of stroke (Hijazi et al., Circulation. 2012; 125:1605-16; Hijazi et al., J Am Coll Cardiol. 2013; 61:2274-84). NT-proBNP has also been shown to be associated with cardio embolic stroke (Llombart et al., B-Type Natriuretic Peptides Help in Cardioembolic Stroke Diagnosis: Pooled Data Meta-Analysis. Stroke. 2015; 46:1187-95). If screening for atrial fibrillation would occur only in individuals with a high level of NT-proBNP some individuals with AF might be missed because of unclear cutoffs a priori, but these might be the individuals with a lower risk of stroke. Furthermore, NT-proBNP levels have been reported to be higher in women than in men in previous studies (Fradley et al, Am J Cardiol. 2011; 108:1341-5; Redfield et al., J Am Coll Cardiol. 2002; 40:976-82). Heavier subjects with higher BMI are more likely to have AF (Wang et al., Jama. 2004; 292:2471-7), but prior studies have also shown an inverse relation between obesity and NT-proBNP (Rivera et al, Eur J Heart Fail. 2005; 7:1168-70; Das et al., Circulation. 2005; 112:2163-8).

A report from the Swedish government agency of Dental and Pharmaceutical Benefits, TLV has recently been published showing that screening for atrial fibrillation using intermittent ECG recordings is cost-effective (Tandvårds-ochläkemedelsförmånsverket. Kunskapsunderlag: Hälsoekonomisk utvärdering gällande primärpreventiv screening av förmaksflimmer med tum-EKG. 2014; http://www.tlv.se/Medicinteknik/Medicinteknikuppdraget/ayslutadehalsoekonomiska-bedomningar/TLV-utvarderar-tum-EKG; 2015 May 29) based on a health-economy study (Aronsson et al., Europace. 2015; 17:48-55). There might also be potential con-founders such as renal failure, as individuals with chronic renal failure have an increased risk of AF (Alonso et al., Circulation. 2011; 123:2946-2953) and higher NT-proBNP (Wang et al., Semin Dial. 2012; 25:326-33).

WO 2014/072500 discloses means and methods for diagnosing a recent paroxysmal atrial fibrillation in a subject, comprising determining the amount of at least one marker selected from the group consisting of a cardiac Troponin, a BNP-type peptide, hsCRP (high sensitive CRP), IL-6 (Interleukin-6) and IGFBP7 (Insulin like growth factor binding protein 7) in a sample from the subject.

An oral presentation was made by Prof. Marten Rosenqvist in Cannes on Apr. 26, 2015 (at the 10th International Biomarker Workshop with 37 participants, Title: "NT-proBNP and silent atrial fibrillation—The STROKESTOP II study"). The presentation dealt with the combined assessment of NT-proBNP and intermittent ECG recordings in the general population.

The technical problem underlying the present invention can be seen as the provision of methods for complying with the aforementioned needs. The technical problem is solved by the embodiments characterized in the claims and herein below.

DETAILED DESCRIPTION

It was found in the context of the studies of the present invention that the determination of the amount of a BNP-type peptide such as NT-proBNP in a sample from a subject with no known history of atrial fibrillation in combination with the assessment of intermittent ECG recordings obtained from said subject over a period of at least one week by using a handheld ECG device allows for an improved assessment of atrial fibrillation. The combination of BNP-type peptide measurements and intermittent ECG recordings is characterized by high sensitivity and high negative predictive value (see Examples). Thanks to the present invention unnecessary health care costs can be avoided.

Accordingly the present invention relates to a method for diagnosing whether a subject with no known history of atrial fibrillation is suffering from atrial fibrillation (AF), said method comprising the steps of
  (a) determining the amount of a BNP-type peptide in a sample of said subject;
  (b) comparing the amount of the BNP-type peptide to a reference, and
  (c) assessing intermittent ECG recordings obtained from said subject over a period of at least one week by using a handheld ECG device.

In an embodiment, the diagnosis is based on the results of the comparison step (b) and the assessment step (c). Thus, the method of the present invention can comprise the further step (d) of diagnosing atrial fibrillation based on the results of steps (b) and (c).

Moreover, the method of the present invention may comprise steps in addition to those explicitly mentioned above. For example, further steps may relate to sample pre-treatments or evaluation of the results obtained by the method. The method may be carried out manually or assisted by automation. Preferably, step (a), (b), (c) and/or (d) may in total or in part be assisted by automation, e.g., by a suitable robotic and sensory equipment for the determination in step (a).

The term "atrial fibrillation" is well known in the art. As used herein, the term refers to a supra-ventricular tachyarrhythmia characterized by uncoordinated atrial activation with consequent deterioration of atrial mechanical function. In particular, the term refers to an abnormal heart rhythm characterized by rapid and irregular beating. It involves the two upper chambers of the heart. In a normal heart rhythm, the impulse generated by the sino-atrial node spreads through the heart and causes contraction of the heart muscle and pumping of blood. In atrial fibrillation, the regular electrical impulses of the sino-atrial node are replaced by disorganized, rapid electrical impulses which result in irregular heart beats. Symptoms of atrial fibrillation are heart palpitations, fainting, shortness of breath, or chest pain. However, most episodes have no symptoms. On the electrocardiogram atrial fibrillation is characterized by the replacement of consistent P waves by rapid oscillations or fibrillatory waves that vary in amplitude, shape, and timing, associated with an irregular, frequently rapid ventricular response when atrioventricular conduction is intact.

Figure 3:
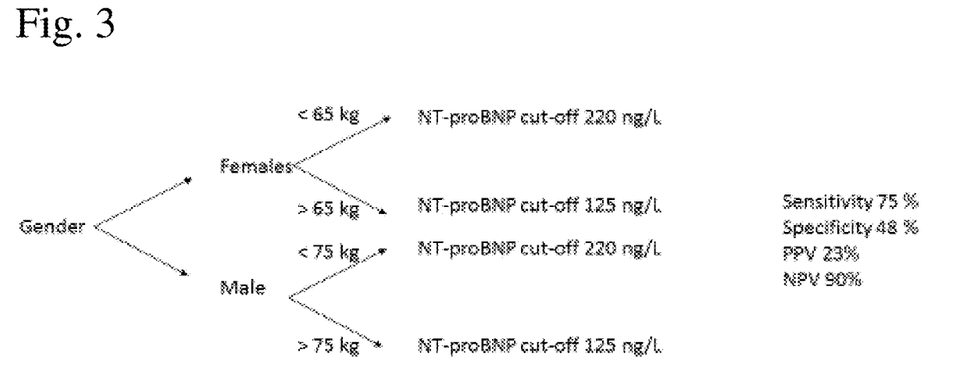
FIG. 3: Model of weight-adjusted NT-proBNP cut-off for AF screening using intermittent ECG recordings. When using weight adjusted NT-proBNP levels, sensitivity remained 75%, specificity 48%, and negative predictive value (NPV) 90%.
Figure 4:
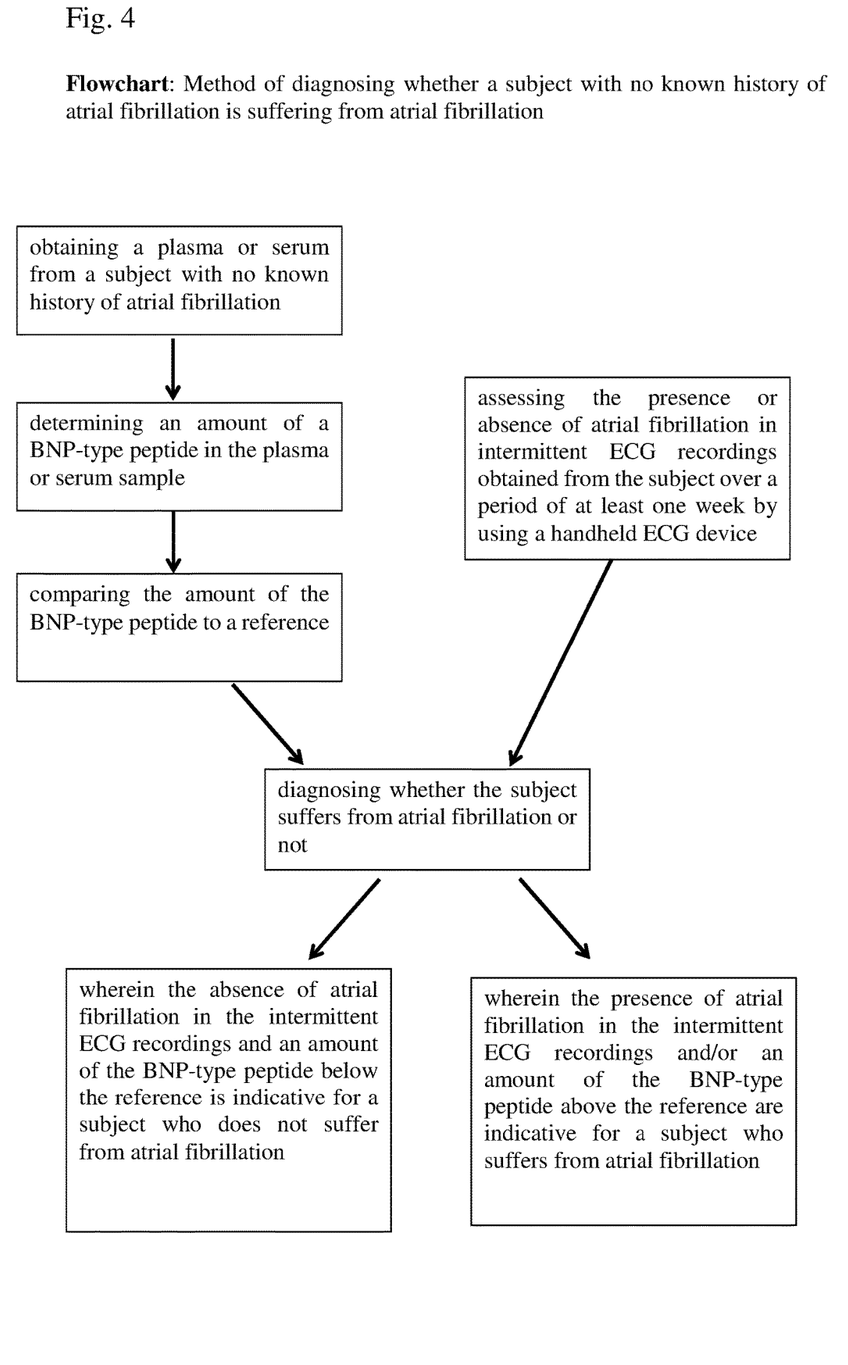
FIG. 4: Flow chart showing the steps of determining the amount of a BNP-type peptide in a sample of a subject, comparing the amount of the BNP-type peptide to a reference, assessing intermittent ECG recordings obtained from said subject over a period of at least one week by using a handheld ECG device, and diagnosing whether the subject suffers from atrial fibrillation or not.

The American College of Cardiology (ACC), American Heart Association (AHA), and the European Society of Cardiology (ESC) propose the following classification system (see Fuster (2006) Circulation 114 (7): e257-354 which herewith is incorporated by reference in its entirety, see e.g. FIG. 3 in the document): First detected AF, paroxysmal AF, persistent AF, and permanent AF.

All people with AF are initially in the category called first detected AF. However, the subject may or may not have had previous undetected episodes. A subject suffers from permanent AF, if the AF has persisted for more than one year. In particular, conversion back to sinus rhythm does not occur (or only with medical intervention). A subject suffers from persistent AF, if the AF lasts more than 7 days. The subject may require either pharmacologic or electrical intervention to terminate atrial fibrillation. Thus persistent AF occurs in episodes, but the arrhythmia does not convert back to sinus rhythm spontaneously. Paroxysmal atrial fibrillation, preferably, refers to an intermittent episode of atrial fibrillation which lasts up to 7 days. In most cases of paroxysmal AF, the episodes last less than 24 hours. The episode of atrial fibrillation terminates spontaneously, i.e. without medical intervention. Both persistent and paroxysmal AF may be recurrent.

The "subject" as referred to herein is, preferably, a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In an embodiment, the subject is a human subject. The subject can be male or female.

In an embodiment, the subject to be tested is not obese. A subject who is not obese usually has a Body Mass Index (BMI) of lower than 30.

In an embodiment of the method of the present invention, the subject is at risk for atrial fibrillation. For example, it is envisaged that the subject to be tested is 65 years of age or older, 70 years of age or older, or 75 years of age or older.

In an embodiment of the present invention, the subject does not have a known history of atrial fibrillation. Accordingly, the subject shall not have been diagnosed to suffer from atrial fibrillation previously, i.e. before carrying out the method of the present invention (in particular before obtaining the sample from the subject and/or before initiating the intermittent ECG recordings). However, the subject may or may not have had previous undiagnosed episodes of atrial fibrillation.

In an embodiment, the subject does not suffer from heart failure and/or does not show overt symptoms of heart failure. The term "heart failure" as used herein refers to an impaired systolic and/or diastolic function of the heart being accompanied by overt signs of heart failure as known to the person skilled in the art. Heart failure according to the present invention includes overt and/or advanced heart failure. Thus, the subject shall not suffer from overt and/or advanced heart failure. In overt heart failure, the subject shows symptoms of heart failure as known to the person skilled in the art.

In an embodiment, the subject does not suffer from heart failure classified as stage C or D of the ACC/AHA classification. In these stages, the subject shows typical symptoms of heart failure, i.e. the subject is not apparently healthy. The subject having heart failure and being classified into stage C or D has undergone permanent, non reversible structural and/or functional changes to his myocardium. However, it is possible that the subject to be tested suffers from heart failure classified as stage A or B of the ACC/AHA classification.

The ACC/AHA classification is a classification for heart failure developed by the American College of Cardiology and the American Heart Association (see J. Am. Coll. Cardiol. 2001; 38; 2101-2113, updated in 2005, see J. Am. Coll. Cardiol. 2005; 46; e1-e82). Four stages A, B, C and D are defined. Stages A and B are not HF (heart failure) but are considered to help identify patients early before developing "truly" HF with clinical signs and symptoms. Stages A and B patients are best defined as those with risk factors for the development of HF (stage A) and structural heart disease without signs or symptoms of HF (stage B), respectively. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate LV hypertrophy (LVH, a phenomenon in which the walls of the ventricle thicken) and/or impaired LV function would be designated as stage B. Stage C then denotes patients with current or past symptoms of HF associated with underlying structural heart disease (the bulk of patients with HF), and stage D designates patients with truly refractory HF.

The term "sample" refers to a sample of a body fluid, to a sample of separated cells or to a sample from a tissue or an organ. Samples of body fluids can be obtained by well-known techniques and include samples of blood, plasma, serum, urine, lymphatic fluid, sputum, ascites, or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

In an embodiment, the sample is a blood (i.e. whole blood), serum or plasma sample. Serum is the liquid fraction of whole blood that is obtained after the blood is allowed to clot. For obtaining the serum, the clot is removed by centrifugation and the supernatant is collected. Plasma is the acellular fluid portion of blood. For obtaining a plasma sample, whole blood is collected in anticoagulant-treated tubes (e.g. citrate-treated or EDTA-treated tubes). Cells are removed from the sample by centrifugation and the supernatant (i.e. the plasma sample) is obtained.

In an embodiment, the term "diagnosing" as used herein means assessing whether a subject as referred to in accordance with the method of the present invention suffers from atrial fibrillation (AF), or not. In particular, the term refers to the assessment of the probability of the subject to suffer from AF, or not. Thus, it is assessed whether a subject has a low or a high probability of suffering from AF. A subject who is diagnosed to suffer from AF shall have a high probability of suffering from AF (such as a probability of about 80% or more). A subject who is diagnosed not to suffer from AF shall have a low probability of suffering from AF (such as a probability of about 15% or less than 15%).

In an embodiment, the method of the present invention allows for making the diagnosis with a negative predictive value of at least about 85%, in particular with a negative predictive value of about 85% to about 95%. Further, it is envisaged that method of the present invention shall allow for making the diagnosis with a positive predictive value of at least about 80%, or of at least about 85%. In an embodiment, the positive predictive value is between about 80% and about 90%, in particular between 85% and 90%.

In a preferred embodiment, it is diagnosed that the subject does not suffer from atrial fibrillation. Thus, the probability of the subject of not suffering from AF is determined/assessed.

As will be understood by those skilled in the art, the diagnosis described herein is usually not intended to be correct for all (i.e. 100%) of the subjects to be diagnosed. The term, however, requires that a statistically significant portion of subjects can be correctly diagnosed (e.g., a cohort in a cohort study). Whether a portion is statistically significant can be determined without further ado by the person skilled in the art using various well-known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly diagnosed by the method of the present invention.

The term "determining" the amount of a BNP-type peptide, refers to the quantification of the biomarker, e.g. to determining the level of the biomarker in the sample, employing appropriate methods of detection described elsewhere herein. The terms "measuring" and "determining" are used herein interchangeably (in connection with biomarkers).

In an embodiment, the amount of a biomarker is determined by contacting the sample with an agent that specifically binds to the biomarker, thereby forming a complex between the agent and said biomarker, detecting the amount of complex formed, and thereby measuring the amount of said biomarker.

A BNP-type peptide can be detected using methods generally known in the art. Methods of detection generally encompass methods to quantify the amount of a biomarker in the sample (quantitative method). It is generally known to the skilled artisan which of the following methods are suitable for qualitative and/or for quantitative detection of a biomarker. Samples can be conveniently assayed for, e.g., proteins using Westerns and immunoassays, like ELISAs, RIAs, fluorescence- and luminescence-based immunoassays, which are commercially available. Further suitable methods to detect a biomarker include measuring a physical or chemical property specific for the peptide or polypeptide such as its precise molecular mass or NMR spectrum. Said methods comprise, e.g., biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

For the detection of biomarker proteins as referred to herein a wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful immunoassays.

Methods employing electrochemiluminescent labels are well-known. Such methods make use of the ability of special metal complexes to achieve, by means of oxidation, an excited state from which they decay to ground state, emitting electrochemiluminescence. For review see Richter, M. M., Chem. Rev. 104 (2004) 3003-3036.

In an embodiment, the detection antibody (or an antigen-binding fragment thereof) to be used for measuring the amount of a biomarker is ruthenylated or iridinylated. Accordingly, the antibody (or an antigen-binding fragment thereof) shall comprise a ruthenium label. In an embodiment, said ruthenium label is a bipyridine-ruthenium (II) complex. Or the antibody (or an antigen-binding fragment thereof) shall comprise an iridium label. In an embodiment, said iridium label is a complex as disclosed in WO 2012/107419.

Measuring the amount of a polypeptide (such as a BNP-type peptide) may, preferably, comprise the steps of (a) contacting the polypeptide with an agent that specifically binds said polypeptide (b) (optionally) removing non-bound agent, (c) measuring the amount of bound binding agent, i.e. the complex of the agent formed in step (a). According to a preferred embodiment, said steps of contacting, removing and measuring may be performed by an analyzer unit. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The agent which specifically binds the biomarker (herein also referred to as "binding agent") may be coupled covalently or non-covalently to a label allowing detection and measurement of the bound agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of tertiary binding agent binding to the secondary binding agent. Suitable secondary and higher order binding agents may include antibodies, secondary antibodies, and the well-known streptavidin-biotin system (Vector Laboratories, Inc.). The binding agent or substrate may also be "tagged" with one or more tags as known in the art. Such tags may then be targets for higher order binding agents. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium complexes, iridium complexes, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, avail-able as ready-made stock solution from Roche Diagnostics), CDP-Star™ (Amersham Bio-sciences), ECF™ (Amersham Biosciences). A suitable enzyme-substrate combination may result in a colored reaction product, fluorescence or chemoluminescence, which can be measured according to methods known in the art (e.g. using a light-sensitive film or a suit-able camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. A radioactive label can be detected by any method known and appropriate, e.g. a light-sensitive film or a phosphor imager.

The amount of a polypeptide may be, also preferably, measured as follows: (a) contacting a solid support comprising a binding agent for the polypeptide as described elsewhere herein with a sample comprising the peptide or polypeptide and (b) measuring the amount peptide or polypeptide which is bound to the support. Materials for manufacturing supports are well-known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc.

In yet an aspect the sample is removed from the complex formed between the binding agent and the at least one marker prior to the measurement of the amount of formed complex. Accordingly, in an aspect, the binding agent may be immobilized on a solid support. In yet an aspect, the sample can be removed from the formed complex on the solid support by applying a washing solution.

"Sandwich assays" are among the most useful and commonly used assays encompassing a number of variations of the sandwich assay technique. Briefly, in a typical assay, an unlabeled (capture) binding agent is immobilized or can be immobilized on a solid substrate, and the sample to be tested is brought into contact with the capture binding agent. After a suitable period of incubation, for a period of time sufficient to allow formation of a binding agent-biomarker complex, a second (detection) binding agent labeled with a reporter molecule capable of producing a detectable signal is then added and incubated, allowing time sufficient for the formation of another complex of binding agent-biomarker-labeled binding agent. Any unreacted material may be washed away, and the presence of the biomarker is determined by observation of a signal produced by the reporter molecule bound to the detection binding agent. The results may either be qualitative, by simple observation of a visible signal, or may be quantitated by comparison with a control sample containing known amounts of biomarker.

The incubation steps of a typical sandwich assay can be varied as required and appropriate. Such variations include for example simultaneous incubations, in which two or more of binding agent and biomarker are co-incubated. For example, both, the sample to be analyzed and a labeled binding agent are added simultaneously to an immobilized capture binding agent. It is also possible to first incubate the sample to be analyzed and a labeled binding agent and to thereafter add an antibody bound to a solid phase or capable of binding to a solid phase.

The formed complex between a specific binding agent and the biomarker shall be proportional to the amount of the biomarker present in the sample. It will be understood that the specificity and/or sensitivity of the binding agent to be applied defines the degree of proportion of at least one marker comprised in the sample which is capable of being specifically bound. Further details on how the measurement can be carried out are also found elsewhere herein. The amount of formed complex shall be transformed into an amount of the biomarker reflecting the amount indeed present in the sample.

The terms "binding agent", "specific binding agent", "analyte-specific binding agent", "detection agent" and "agent that specifically binds to a biomarker" are used interchangeably herein. Preferably it relates to an agent that comprises a binding moiety which specifically binds the corresponding biomarker. Examples of "binding agents" or "agents" are a nucleic acid probe, nucleic acid primer, DNA molecule, RNA molecule, aptamer, antibody, antibody fragment, peptide, peptide nucleic acid (PNA) or chemical compound. A preferred agent is an antibody which specifically binds to the biomarker to be measured. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity (i.e. antigen-binding fragments thereof). Preferably, the antibody is a polyclonal antibody. More preferably, the antibody is a monoclonal antibody.

The term "specific binding" or "specifically bind" refers to a binding reaction wherein binding pair molecules exhibit a binding to each other under conditions where they do not significantly bind to other molecules. The term "specific binding" or "specifically binds", when referring to a protein or peptide as biomarker, refers to a binding reaction wherein a binding agent binds to the corresponding biomarker with an affinity of at least $10^{-7}$ M. The term "specific binding" or "specifically binds" preferably refers to an affinity of at least $10^{-8}$ M or even more preferred of at least $10^{-9}$ M for its target molecule. The term "specific" or "specifically" is used to indicate that other molecules present in the sample do not significantly bind to the binding agent specific for the target molecule.

The Brain Natriuretic Peptide type peptide (herein also referred to as BNP-type peptide) is preferably selected from the group consisting of pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP). Preferably, brain natriuretic peptides according to the present invention are NT-proBNP, BNP, and variants thereof. BNP is the active hormone and has a shorter half-life than its respective inactive counterpart NT-proBNP. Preferably, the Brain Natriuretic Peptide-type peptide is BNP (Brain natriuretic peptide), and more preferably NT-proBNP (N-terminal of the prohormone brain natriuretic peptide).

The term "amount" as used herein encompasses the absolute amount of a BNP-type peptide, the relative amount or concentration of the BNP-type peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts measured from biological read out systems in response to the peptides or intensity signals obtained from specifically bound ligands. It is to be understood that values correlating to the aforementioned amounts or parameters can also be obtained by all standard mathematical operations.

The term "comparing" as used herein refers to comparing the amount of the BNP-type peptide in the sample from the subject with the reference amount of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer-assisted. Thus, the comparison may be carried out by a computing device. The value of the measured or detected amount of the biomarker in the sample from the subject and the reference amount can be, e.g., compared to each other and the said comparison can be automatically carried out by a computer program executing an algorithm for the comparison. The computer program carrying out the said evaluation will provide the desired assessment in a suitable output format. For a computer-assisted comparison, the value of the measured amount may be compared to values corresponding to suitable references which are stored in a database by a computer program. The computer program may further evaluate the result of the comparison, i.e. automatically provide the desired assessment in a suitable output format. For a computer-assisted comparison, the value of the measured amount may be compared to values corresponding to suitable references which are stored in a database by a computer program. The computer program may further evaluate the result of the comparison, i.e. automatically provides the desired assessment in a suitable output format.

In accordance with the present invention the amount of the BNP-type peptide (in particular the amount of the biomarker NT-proBNP) shall be compared to a reference. The reference is preferably a reference amount. The term "reference amount" as used herein refers to an amount which allows (in combination with the ECG recordings) for allocation of a subject into either (i) the group of subjects suffering atrial fibrillation or (ii) the group of subjects not suffering from atrial fibrillation. A suitable reference amount may be determined from a reference sample to be analyzed together, i.e. simultaneously or subsequently, with the test sample.

Reference amounts can, in principle, be calculated for a cohort of subjects as specified above based on the average or mean values for a given biomarker by applying standard methods of statistics. In particular, accuracy of a test such as a method aiming to diagnose an event, or not, is best described by its receiver-operating characteristics (ROC) (see especially Zweig 1993, Clin. Chem. 39:561-577). The ROC graph is a plot of all of the sensitivity versus specificity pairs resulting from continuously varying the decision threshold over the entire range of data observed. The clinical performance of a diagnostic method depends on its accuracy, i.e. its ability to correctly allocate subjects to a certain prognosis or diagnosis. The ROC plot indicates the overlap between the two distributions by plotting the sensitivity versus 1−specificity for the complete range of thresholds suitable for making a distinction. On the y-axis is sensitivity, or the true-positive fraction, which is defined as the ratio of number of true-positive test results to the product of number of true-positive and number of false-negative test results. This has also been referred to as positivity in the presence of a disease or condition. It is calculated solely from the affected subgroup. On the x-axis is the false-positive fraction, or 1−specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/1 specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis for a given event with a proper balance of sensitivity and specificity, respectively. Accordingly, the reference to be used for the aforementioned method of the present invention, i.e. a threshold which allows to differentiating between subjects suffering from atrial fibrillation or those not suffering atrial fibrillation among a cohort of subjects can be generated, preferably, by establishing a ROC for said cohort as described above and deriving a threshold amount therefrom. Dependent on a desired sensitivity and specificity for a diagnostic method, the ROC plot allows deriving a suitable threshold. It will be understood that an optimal sensitivity is desired for excluding a subject suffering from atrial fibrillation (i.e. a rule out) whereas an optimal specificity is envisaged for a subject to be assessed as suffering from atrial fibrillation (i.e. a rule in).

In certain embodiments, the term "reference amount" herein refers to a predetermined value. In an embodiment, said predetermined value shall allow for differentiating between a subject suffering from atrial fibrillation and a subject not suffering from atrial fibrillation (in combination with the results of the ECG recordings). In another embodiment, said reference amount shall allow for diagnosing that a subject does not suffer from atrial fibrillation, i.e. for excluding a subject suffering from atrial fibrillation.

In certain embodiments, the reference amount is derived from a subject or a group of subjects known not to suffer from atrial fibrillation or from a subject or a group of subjects known to suffer from atrial fibrillation.

In an embodiment, the reference subject(s) does (do) not suffer from heart failure, in particular from heart failure classified as stage C or D of the ACC/AHA classification.

In a preferred embodiment, the reference for the BNP-type peptide is an age, gender and/or weight specific reference, in particular an age, gender and/or weight specific reference amount.

For example, different reference amounts may be used for male and female subjects, or for subject having a weight of more than about 65 kg (or 75 kg) and subjects having a weight of less than about 65 kg (or 75 kg).

A typical reference amount indicative for the diagnosis of atrial fibrillation in a male subject having a weight of more than about 75 kg is an amount of about 110 to 140 ng/l, in particular of about 125 ng/l.

A typical reference amount indicative for the diagnosis of atrial fibrillation in a male subject having a weight of less than about 75 kg is an amount of about 200 to 240 ng/l, in particular of about 220 ng/l.

A typical reference amount indicative for the diagnosis of atrial fibrillation in a female subject having a weight of more than about 65 kg is an amount of about 110 to 140 ng/l, in particular of about 125 ng/l.

A typical reference amount indicative for the diagnosis of atrial fibrillation in a female subject having a weight of less than about 65 kg is an amount of about 200 to 240 ng/l, in particular of about 220 ng/l.

The aforementioned amounts are preferably measured with the centralized laboratory test Elecsys® NT proBNPII assay from Roche Diagnostics, Germany and/or related products with same antibody epitope and standardization, such as the Roche CARDIAC proBNP+ on the point of care analyser (Cobas h 232 point-of-care) of Roche.

Preferably, the term "about" as used herein encompasses a range of + and −20% relative to the specific value, amount, concentration, level, etc., e.g., indication of a value of "about 100" is meant to encompass a value of a numerical range of 100+/−20%, i.e., a value range from 80 to 120. Preferably, the term "about" encompasses a range of + and −10% relative to the specific value, amount, concentration, level, etc. and, more preferably, a range of + and −10% relative to the specific value, amount, concentration, level, etc. Most preferably, the term "about" refers to the exact value, amount, concentration, level, etc.

If weight and/or gender specific reference amounts are applied, the method of the present invention might further encompass the step of assessing the weight and/or gender of the subject. Thus, it may be assessed whether a female subject has a weight of less than about 65 kg or more than about 65 kg, and/or whether a male subject has a weight of less than about 75 kg or more than about 75 kg.

The reference amounts referred to above are reference amounts for NT-proBNP in a blood, serum or plasma sample. The application of the gender and/or weight specific reference amounts allows for the diagnosis with a negative predictive value of about 85% or more, in particular or about 90% or more. Thus, it can be reliably diagnosed that the subject does not suffer from AF.

A high negative predictive value indicates a high level of confidence in a negative assessment made by a diagnostic test. The negative predictive value can be expressed as the number of true negative results divided by the sum of the true negative results and the false negative results (i.e. all negative outcomes determined by the diagnostic test). In principle, a negative predictive value can be calculated depending on the sensitivity and specificity of a diagnostic test and the prevalence for a disease or condition in certain cohort. Specifically, the negative predictive value is [(specificity)(1−prevalence)]/[(specificity)(1−prevalence)+(1−sensitivity)(prevalence)].

In an embodiment, the reference amount to be applied shall allow for making the diagnosis (in particular the diagnosis that the subject does not suffer from AF) with a negative predictive value of at least about 85%.

Further, it is envisaged that the reference amount to be applied shall allow for making the diagnosis with a positive predictive value of at least about 80%, or of at least about 85%.

Further positive and negative predictive values that can be achieved using the present invention are disclosed elsewhere herein.

In step (c) of the method of the present invention, intermittent ECG recordings from the subject to be tested shall be assessed. Said intermittent ECG recordings shall have been obtained from said subject over a period of at least one week by using a handheld ECG device.

Electrocardiography (abbreviated ECG) is the process of recording the electrical activity of the heart. An ECG device records the electrical signals produced by the heart which spread throughout the body to the skin. The recording is of the electrical signal is achieved by contacting the skin of the test subject with electrodes comprised by the ECG device. The process of obtaining the recording is non-invasive and risk-free.

In accordance with the present invention the recordings obtained with a handheld ECG device shall be assessed. The expression "assessing intermittent ECG recordings" as used herein preferably refers to assessing the presence or absence of atrial fibrillation in the intermittent ECG recordings (i.e. ECG readings/ECG strips) obtained from the subject. Thus, the recordings are interpreted. Said assessment can be carried out by a physician such as a cardiologist and/or computer-assisted. For example, a pre-assessment can be done by an automated software. The final assessment of the pre-assessed results can be carried out by a physician.

The handheld ECG device as referred to in step c) of the method of the present invention thus shall allow for the diagnosis of atrial fibrillation, i.e. for the assessment of the presence of absence of atrial fibrillation (in the ECG recordings obtained from the subject).

Handheld ECG devices which allow for the diagnosis of are produced by various manufacturers. Examples are the AfibAlert® from Lohman Technologies a device specifically targeting the detection of atrial fibrillation, the Zenicor-ECG from Zenicor, Sweden, the AliveCor Mobile ECG, the Dimetek Micro Ambulatory ECG Recorder, the ECG Check, the HeartCheck™ PEN handheld ECG, the InstantCheck Real Time Display ECG monitor, the ReadMyHeart device, or the REKA E100.

In embodiment of the method of the present invention, the handheld ECG device is a one-lead device. Thus, it is in particular envisaged that the ECG device used for obtaining the intermittent ECG recordings is not a 12-lead ECG device such as a Holter monitor.

In an embodiment of the present invention, the handheld ECG device is a device operated by the subject to be tested. Thus, the handheld device as referred to in the method of the present invention shall allow for self-testing by the test subject. In other words, the recordings to be assessed were obtained by self-testing.

In accordance with the present invention, it is envisaged that the handheld ECG device comprises two dry-contact electrodes. Thus, it is contemplated that the intermittent ECG recordings have been obtained by placing two fingers (such as the left and right thumb) on the dry-contact electrodes. Alternatively, the dry-contact electrodes can by place against the bare skin such as the chest.

The ECG recordings in step b) are intermittent ECG recordings. Thus, the ECG recordings shall not have been obtained continuously from the subject (which is e.g. the case for Holter monitoring). Accordingly, the ECG recordings to be assessed are recordings that were obtained periodically over a period of at least one week.

However, it is envisaged that ECG recordings were obtained at least once a day from the subject. The device is thus operated by the subject as least once a day. The expression "at least once" as used herein means once or more than once such as twice, three times, four times, five times etc. In an embodiment, the ECG recordings are obtained twice a day of more. The recordings may be stored or transmitted to a ECG database e.g. via mobile phone that is built in or connected with the ECG device. For example, the ECG device can be connected with a mobile phone (e.g. via a bluetooth or wireless connection) which transfers recordings to the database. The transmission can be achieved via an app (such as an Android or iOS app). After transmission of the recordings to the database, the recordings can be assessed for the presence or absence of atrial fibrillation, i.e. interpreted, by a physician.

The length of a (single) recording is usually between about 10 seconds and about 120 seconds. In an embodiment the length of a recording is between about 20 second and about 60 seconds. For example, a ECG recording may have been obtained by placing the thumbs on the two electrodes for about 30 seconds.

Further, it is in particular envisaged that the intermittent ECG recordings were obtained when the subject shows symptoms of atrial fibrillation (provided that the subject has shown symptoms). Said symptoms are usually transient and may arise in a few seconds and may disappear just as quickly. Symptoms of atrial fibrillation include dizziness, fainting, shortness of breath and, in particular, heart palpitations. Accordingly, the recordings e.g. are obtained when the subject exhibits heart palpitations.

If the subject does not show symptoms of atrial fibrillation, the recordings shall be nevertheless obtained at least once a day as described above.

In an embodiment, the intermittent, i.e. non-continuous, ECG recordings shall have been obtained over a period of at least four days. In another embodiment, the intermittent, i.e. non-continuous, ECG recordings shall have been obtained over a period of at least one week. The intermittent, i.e. non-continuous, ECG recordings shall have been obtained over a period of at least one week. Thus, there shall be at least 7, in particular at least 14 recordings that shall be assessed in step c) of the method of the present invention. In an embodiment, the intermittent ECG recordings shall have been obtained over a period of at least ten days. In another embodiment, the intermittent ECG recordings shall have been obtained over a period of at least two weeks. Further, it is envisaged that the intermittent ECG recordings to be assessed have been obtained over a period of one week to two weeks, in particular over a period of ten days to two weeks. The presence of AF in at least one recording is indicative for the diagnosis of AF.

As set forth above, the diagnosis that the subject suffers from atrial fibrillation or not shall be based on the results of the comparison step b) and the assessment step c).

Typical diagnostic algorithms for various embodiments are described below.

In an embodiment, it is diagnosed that the patient does not suffer from atrial fibrillation. This is indicated by the absence of atrial fibrillation in the intermittent ECG recordings and by an amount of the BNP-type peptide in the sample from the subject below the reference. In other words, the absence of atrial fibrillation in the intermittent ECG recordings in combination with an amount of the BNP-type peptide below the reference are indicative for a subject who does not suffer from atrial fibrillation. Thus, the subject has a low probability of suffering from atrial fibrillation (such as a probability of lower than 10 or 15%).

In an embodiment, it is diagnosed that the patient suffers from atrial fibrillation. This is indicated by the presence of atrial fibrillation in the intermittent ECG recordings (i.e. the presence of atrial fibrillation in at least one recording) and/or by an amount of the BNP-type peptide in the sample from the subject above the reference is indicative. In other words, the presence of atrial fibrillation in the intermittent ECG recordings and/or an amount of the BNP-type peptide above the reference are indicative for a subject who suffers from atrial fibrillation. Thus, the subject has a high probability of suffering from atrial fibrillation (such as a probability of higher than 70 or 80%).

The absence of atrial fibrillation in the intermittent ECG recordings from the subject in combination with an amount of the BNP-type peptide above the reference might be indicative for a subject who suffers from atrial fibrillation. Although, no atrial fibrillation was detected in the ECG, the subject is likely to suffer from atrial fibrillation. However, this shall be confirmed by continuously monitoring electrical activity of the cardiovascular system for at least 24 hours, e.g. by Holter monitoring or by implantable loop recorders (ILR). Accordingly, it is envisaged that the subject is subjected to a further assessment of AF (such as Holter monitoring) if the amount of the BNP is above the reference and no AF was detected in the intermittent ECG recordings. The further assessment shall allow for the diagnosis whether the subject suffers from AF or not.

In certain embodiments, the term "above the reference amount" refers to an amount of the biomarker in the sample from the individual or patient above the reference amount or to an overall increase of 5%, 10%, 20%, 25%, 30%, 40%, 50%, 60%, 70%, 80%, 85%, 90%, 95%, 100% or greater, determined by the methods described herein, as compared to the reference amount. In certain embodiments, the term "decrease" or "below" herein refers to an amount of the biomarker in the sample from the individual or patient below the reference amount or to an overall reduction of 5%, 10%, 20%, 25%, 30%, 40%, 50%% or greater, determined by the methods described herein, as compared to the reference amount.

In an embodiment of the method of the invention, said method further comprises a step of recommending and/or initiating at least one suitable supportive measure according to the results of the comparison step b) and the assessment step c). Said at least one suitable supportive measure shall be recommended or initiated is diagnosed to suffer from atrial fibrillation, i.e. has a high probability of suffering from AF.

The term "recommending" as used herein means establishing a proposal for a suitable supportive measure which could be applied to the subject.

The suitable supportive measure refers to all measures which can be applied to subjects suffering from AF, i.e. having a high probability of suffering from AF. For example, patient management measures include the verification of the diagnosis of AF (e.g. by Holter monitoring) and/or drug treatment.

If the subject suffers from atrial fibrillation, a therapy with at least one anticoagulant shall be recommended or initiated. The anticoagulant shall aim to reduce or prevent coagulation of blood and related stroke. In an embodiment, the anticoagulant is selected from the group consisting of heparin, a coumarin derivative, such as warfarin or dicumarol, tissue factor pathway inhibitor (TFPI), antithrombin III, factor IXa inhibitors, factor Xa inhibitors, inhibitors of factors Va and VIIIa, and thrombin inhibitors.

The definitions given herein above apply mutatis mutandis to the following embodiment of the present invention.

The present invention furthermore relates to the use of i) a BNP-type peptide and/or a detection agent which specifically binds thereto (preferably in a sample of subject with no known history of atrial fibrillation) and ii) a handheld ECG device and/or intermittent ECG recordings obtained by using a handheld ECG device from a subject with no known history of atrial fibrillation for diagnosing whether said subject suffers from atrial fibrillation or not.

In an embodiment, the detection agent is a polyclonal or monoclonal antibody (or antigen-binding fragment thereof) which specifically binds to said BNP-type peptide.

EMBODIMENTS OF THE INVENTION

1. A method of diagnosing whether a subject with no known history of atrial fibrillation is suffering from atrial fibrillation or not, said method comprising the steps of
   a) determining the amount of a BNP-type peptide in a sample of said subject;
   b) comparing the amount of the BNP-type peptide to a reference, and
   c) assessing intermittent ECG recordings obtained from said subject over a period of at least one week by using a handheld ECG device.
2. The method of embodiment 1, wherein the BNP-type peptide is NT-proBNP or BNP.
3. The method of embodiments 1 and 2, wherein the sample is blood, serum or plasma.
4. The method of any one of embodiments 1 to 3, wherein the handheld ECG device is a one-lead device.
5. The method of any one of embodiments 1 to 4, wherein the handheld ECG device is operated by the subject to be tested.
6. The method of any one of embodiments 1 to 5, wherein the handheld ECG device comprises two dry-contact electrodes.
7. The method according to embodiment 6, wherein the intermittent ECG recordings are obtained by placing the thumbs on the dry-contact electrodes.
8. The method according to any one of embodiments 1 to 7, wherein the intermittent ECG recordings are obtained at least once daily or at least twice daily.
9. The method according to any one of embodiments 1 to 8, wherein the intermittent ECG recordings are obtained when the subject shows symptoms of atrial fibrillation.
10. The method according to any one of embodiments 1 to 9, wherein the subject is 70 years of age or older.
11. The method according to any one of embodiments 1 to 10, wherein it is diagnosed that the patient does not suffer from atrial fibrillation.
12. The method of embodiment 11, wherein the absence of atrial fibrillation in the intermittent ECG recordings and an amount of the BNP-type peptide below the reference is indicative for a subject who does not suffer from atrial fibrillation.
13. The method according to any one of embodiment 1 to 11, wherein the reference for the BNP-type peptide is an age, gender and/or weight specific reference.
14. Use of i) a BNP-type peptide and/or a detection agent which specifically binds thereto and ii) a handheld ECG device and/or intermittent ECG recordings obtained by using a handheld ECG device from a subject with no known history of atrial fibrillation for diagnosing whether said subject suffers from atrial fibrillation or not.
15. Use of embodiment 14, wherein the detection agent is an antibody or antigen-binding fragment thereof which specifically binds to said BNP-type peptide.

All references cited in this specification are herewith incorporated by reference with respect to their entire disclosure content and the disclosure content specifically mentioned in this specification.

EXAMPLES

The invention will be merely illustrated by the following Examples. The said Examples shall, whatsoever, not be construed in a manner limiting the scope of the invention.

Example 1: Systematic ECG Screening for Untreated Atrial Fibrillation (AF)—Study Design and Setup The design of the STROKESTOP study has been published previously (Friberg L et al., Europace. 2013; 15:135-40). In short, all individuals (n=28'768) aged 75 or 76 residing in two Swedish regions were randomized in a 1:1 fashion to a control group or invited to screening for AF. In the screening group, 7'173 individuals (54%) attended screening. They were asked to fill out a health questionnaire detailing their co-morbidities enabling calculation of stroke risk according to the $CHA_2DS_2$-VASc score (Camm et al., Eur Heart J. 2012; 33:2719-47), if they had ever been diagnosed with AF before, and if they were on current treatment with OAC or a platelet inhibitor. In the Stockholm region, participants were asked to report self-estimated height and weight.

Individuals without known AF were equipped with a handheld one-lead device (www.zenicor.com) for intermittent ECG recordings twice daily during two weeks. The device has an integrated mobile transmitter that sends 30 second ECG strips to a database. This device has been extensively validated in prior studies, and has been shown to be superior to 24-h Holter recordings for detection of AF ENREF 14 (Doliwa et al., Scand Cardiovasc J. 2009; 43:163-8; Doliwa et al., Scand Cardiovasc J. 2012; 46:144-8; Doliwa et al., Europace. 2012; 14:1112-1116; Orrsj et al., ISRN Stroke. 2014; 2014:6). Compliance to ECG registration was good, with an average of 26.4 ECGs/participant. If intermittent ECG recordings were difficult to interpret additional assessment using long term ECG recordings, such as 24-h Holter, were performed. All individuals with newly diagnosed AF (NDAF), and AF patients not treated with OACs, were offered a structured follow-up by a cardiologist to ensure adequate treatment, according to current European guidelines (Camm et al., Eur Heart J. 2010; 31:2369-429).

In the last 815 consecutive participants attending screening a sample of NT-proBNP was taken and analysed beside using a point of care analyser (Cobas 232 point-of-care) by Roche (Bertsch et al., Clin Lab. 2010; 56:37-49). In addition 71 individuals with NDAF had NT-proBNP taken at cardiology follow-up (Immulite 2000 XPI). Participants that had a NT-proBNP level exceeding 9 000 ng/L were referred to a cardiologist for further work-up. The investigators interpreting the ECGs were blinded to NT-proBNP levels.

Statistics

Shapiro-Wilk's test and a visual inspection of histograms showed that NT-proBNP data were positively skewed, and not normally distributed across all groups. Non-parametric tests were used, for independent samples Mann-Whitney U or Kruskal-Wallis as appropriate. Chi-square, Fisher's exact test and student t-test were used to compare differences between groups. Data are described as median and interquartile range (with percentiles calculated using weighted average). A two-sided $p<0.05$ was deemed as significant. Multivariable analysis was performed using binary logistic regression. The discriminative ability of the model was estimated as c-statistics.

Ethics

The study complies with the Declaration of Helsinki, and the protocol was approved by the regional ethics committee (DNR 2011-1363-31/3). Informed consent was obtained from all participants in the screening program. ClinicalTrials.gov identifier: NCT01593553.

Example 2: Results of the Mass Screening Study in Relation to NT-proBNP

A total of 886 individuals within the systematic ECG screening study for Atrial Fibrillation had NT-proBNP analysed. The clinical characteristics included in the $CHA_2DS_2$-VASc score did not differ significantly between the groups with newly discovered AF (NDAF) compared to those without detectable AF, see Table 1.

TABLE 1

Baseline characteristics in participants per diagnosis. Missing data not reported (sum in rows might < total).

|  | New AF (n = 96) | | No AF (n = 742) | | p (New vs No) | Known AF (n = 48) | |
| --- | --- | --- | --- | --- | --- | --- | --- |
| Median NT-proBNP, ng/L | 330 | | 171 | | <0.001 | 472* | |
| IQR | 510 | (124; 634) | 188 | (95; 283) | | 983 | (187; 1170) |
| Congestive Heart Failure, n (%) | 1 | (1.1%) | 19 | (2.6%) | 0.718 | 9 | (19.6%)* |
| Hypertension, n (%) | 54 | (56.3%) | 354 | (48.1%) | 0.13 | 23 | (50%) |
| Diabetes Mellitus, n (%) | 14 | (14.6%) | 85 | (11.5%) | 0.38 | 4 | (8.3%) |
| Prior Stroke/TIA, n (%) | 9 | (9.4%) | 73 | (10.0%) | 0.85 | 8 | (16.7%) |
| Vascular disease, n (%) | 14 | (14.6%) | 73 | (10.0%) | 0.16 | 6 | (12.5%) |
| Female gender, n (%) | 39 | (41.1%) | 327 | (44.2%) | 0.56 | 12 | (25.5%)† |
| $CHA_2DS_2$-VASc mean (95% c.i) | 3.46 | (3.24-3.68) | 3.35 | (3.27-3.43) | 0.30 | 3.46 | (3.07-3.84) |
| $CHA_2DS_2$-VASc median | 3 | (IQR 3; 4) | 3 | (IQR 3; 4) | | 3 | (IQR 2; 4) |
| Height, cm (n = 478) | 173.3 | (CI 171.5-175.1) | 171.6 | (CI 170.7-172.5) | 0.099 | 177.6 | (169.4-185.8) NS |
| Weight, kg | 83.3 | (78.8-87.9) | 75.7 | (74.4-77.0) | 0.002 | 81.1 | (69.6-92.6) NS |
| BMI | 27.8 | (26.2-29.5) | 25.7 | (25.3-26.1) | 0.014 | 25.6 | (23.2-28.1) NS |

TIA = transient ischaemic attack,
BMI = Body Mass Index.
*p < 0.001 compared to no AF, p < 0.05 compared to new AF †p < 0.05 compared to no AF (NS compared to new AF)

Individuals with NDAF (n=96) had a NT-proBNP median of 330 ng/L (interquartile range [IQR] 121; 634) whereas individuals without AF (n=742) had a NT-proBNP median of 171 ng/L (IQR 95; 283, p<0.001) and individuals with previously diagnosed AF, n=48, had a NT-proBNP median of 472 ng/L (IQR 184; 1186, p<0.05 for both comparisons). Individuals with a prior diagnosis of AF had a mean $CHA_2DS_2$-VASc score 3.46 (CI 3.07-3.84) that did not differ from individuals with NDAF (CI 3.24-3.68), although they had a higher prevalence of heart failure than both individuals with NDAF and individuals without AF (p<0.001).

There was a significantly lower proportion of women in the group with a previous diagnosis of AF than in the group without AF (p=0.012), but no other clinical parameters differed.

Information about height and weight was obtained from 478 individuals. Individuals with NDAF were heavier than individuals without AF (83.3 kg vs 75.7 kg, p=0.002). See Table 1.

There were no significant gender differences in NT-proBNP levels regardless of AF status.

NT-proBNP was analysed using two different methods. The majority (n=815) underwent point of care testing at the first screening visit, and in addition 71 patients had NT-proBNP taken at follow-up. However, the significant difference in NT-proBNP between participants with NDAF and without AF remained (p=0.047) whether or not the participants with NT-proBNP taken at follow-up were included.

NT-proBNP Excluding Heart Failure

NT-proBNP median in individuals with NDAF remained increased as compared to individuals without AF even if the 29 individuals with previously known heart failure were excluded; 328 ng/L (IQR 118; 632) vs 166 ng/L (IQR 94; 276) (p<0.001).

Individuals with a prior diagnosis of AF had higher NT-proBNP levels than individuals without AF (median 421 ng/L vs 166 ng/L, p<0.001). This was true even if patients with heart failure were excluded. However, the difference in NT-proBNP levels between participants with NDAF and previously known AF disappeared after exclusion of patients with known heart failure.

NT-proBNP and Type of AF

The majority of the 96 individuals with NDAF discovered during screening, had paroxysmal AF detected using intermittent ECGs (n=61), or other types of long term ECGs (n=16). Individuals who were in AF on the first visit, n=18, were more likely to have permanent/persistent arrhythmias.

Individuals with AF detected at first medical contact (n=18) had a higher NT-proBNP level than individuals with paroxysmal AF (median 847 vs 225 ng/L, p<0.001).

Figure 1:
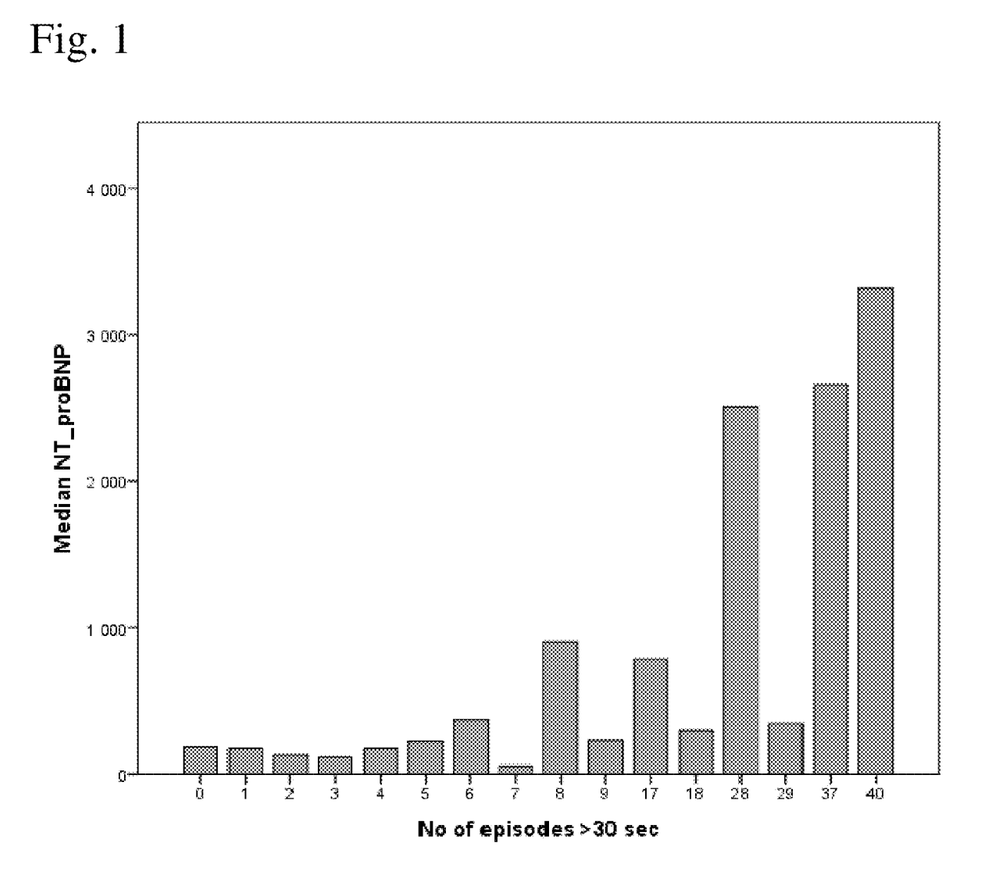
FIG. 1: Number of AF episodes detected on intermittent ECG recordings in STROKESTOP participants with newly detected AF depicted on x-axis. Median level of NT-proBNP in ng/L is shown on the Y-axis. Participants with newly detected AF who had more frequent AF episodes on their intermittent ECG recordings had higher levels of NT-proBNP than those with few episodes.

Participants with NDAF who had more frequent AF episodes on their intermittent ECG recordings had higher levels of NT-proBNP than those with few episodes, FIG. 1.

Participants with arrhythmias discovered on the first ECG, "index ECG" are likely to have permanent AF, and had significantly higher levels of NT-proBNP compared to participants with paroxysmal AF episodes. These findings are in accordance with findings from the ARISTOTLE study (Hijazi et al., J Am Coll Cardiol. 2013; 61:2274-84). Participants with more episodes of AF during intermittent ECG recordings had higher NT-proBNP levels than participants with few episodes. As continuous monitoring was not used the exact AF burden was not possible to assess, but participants with several registered AF episodes were more likely to have a high AF burden compared to participants with fewer registered AF episodes.

NT-proBNP as a Predictor for Development of AF

Figure 2:
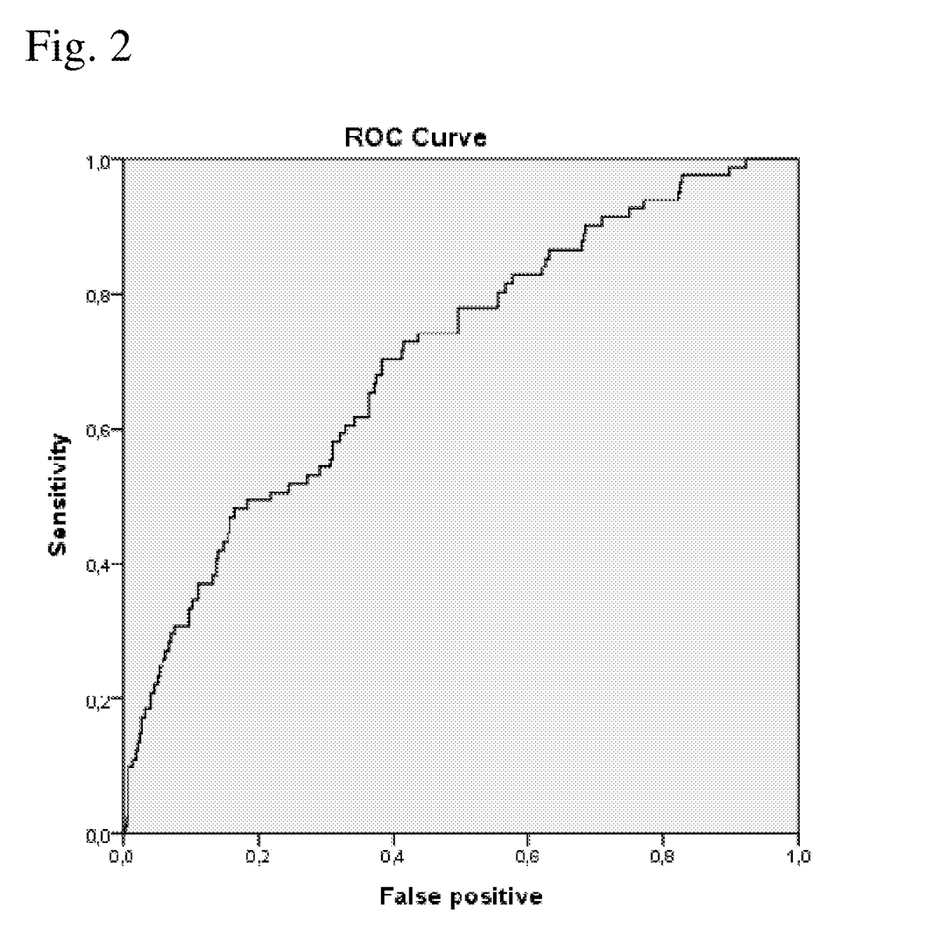
FIG. 2: ROC-curve depicting detection of new AF as a function of Weight and NT-proBNP. The c-statistic (area under the ROC curve) increased to 0.71 (confidence interval [CI] 0.64-0.77) when detection of new AF was depicted as a function of Weight and NT-proBNP, compared to NT-proBNP alone (c-statistic 0.64 (confidence interval [CI] 0.57-0.71)).

Using binary logistic regression unadjusted odds ratios for the likelihood of detecting new AF were non-significant for all clinical parameters included in the $CHA_2DS_2$-VASc, whereas NT-proBNP was significantly associated with AF. This association remained significant after multivariable adjustments (Table 2). Adding height and weight in a second step of the multivariable analysis showed that for every increase of 1 kg in weight the odds ratio (OR) was 1.03 (95% confidence interval [CI] 1.01-1.05, p<0.001) and for height (1 cm increase) OR was 1.05 (1.0-1.1, p=0.04). NT proBNP remained significant (p<0.001). The c-statistic for NT-proBNP alone was 0.64 (CI 0.57-0.71). Adding NT-proBNP to weight increased the c-statistic to 0.71 (CI 0.64-0.77) (FIG. 2).

TABLE 2

Univariate and multivariable analysis for newly detected AF.

| Variable | Unadjusted OR (95% CI) | p-value | Adjusted OR (95% CI) | p-value |
|---|---|---|---|---|
| Heart Failure (Yes) | 0.40 (0.05-3) | 0.376 | 0.19 (0.02-1.63) | 0.130 |
| Hypertension (Yes) | 1.39 (0.91-2.13) | 0.134 | 1.38 (0.88-2.18) | 0.150 |
| Diabetes Mellitus (Yes) | 1.31 (0.71-2.42) | 0.381 | 1.05 (0.54-2.04) | 0.897 |
| Prior stroke/TIA (Yes) | 0.93 (0.45-1.93) | 0.851 | 0.68 (0.30-1.53) | 0.355 |
| Vascular disease (Yes) | 1.54 (0.83-2.86) | 0.167 | 1.21 (0.60-2.44) | 0.596 |
| Gender (female) | 0.88 (0.57-1.36) | 0.562 | 0.88 (0.55-1.39) | 0.571 |
| NT-proBNP, ng/L | 1.001 (1.001-1.001) | <0.001 | 1.001 (1.001-1.002) | <0.001 |

OR = odds ratio
TIA = transient ischaemic attack.

Using receiver operating characteristic regression (ROC-curves) to determine a cut-off level for NT-proBNP for AF screening, a value of 125 ng/L was considered as an optimal level. Using a cut-off of NT-proBNP of 125 ng/1 one would have found 72/96 new AF patients, hence sensitivity is 75%, specificity is 38%. The negative predictive value of NT-proBNP<125 ng/L is 92%.

NT-proBNP levels are lower in obese individuals (Das et al., Circulation. 2005; 112:2163-8), but the physiological mechanism for this remains unclear (Madamanchi et al., International Journal of Cardiology. 2014; 176:611-617). This suggests that a weight adjusted NT-proBNP could be used in order to improve screening, as depicted in FIG. 3. Using weight adjusted NT-proBNP levels, the sensitivity remained 75%, specificity 48%, and NPV 90%. Using a body weight adjusted NT-proBNP cut-off fewer individuals would need to go through AF screening with intermittent ECG recordings.

Risk scores for prediction of AF have been evaluated previously in other cohorts (Alonso et al., J Am Heart Assoc. 2013; 2:e000102; Schnabel et al., Lancet. 2009; 373:739-45). The Cohorts for Heart and Aging Research in Genomic Epidemiology (CHARGE)-AF consortium developed a risk score using several clinical parameters. Using weight, height, history of hypertension, history of diabetes, congestive heart failure and vascular disease we made a similar model. Only weight came out as significantly associated with the detection of new AF, p=0.002. C-statistics for this risk score was 0.64 (CI 0.58-0.71). Adding NT-proBNP to the score increased the C-statistics of the adjusted CHARGE-AF score to 0.72 (CI 0.66-0.78).

This increase in C-statistics using NT-proBNP could help discern subjects who are more likely to develop AF and thus are more likely to benefit from participation in a screening program.

The invention claimed is:

1. A method of diagnosing whether a subject with no known history of atrial fibrillation is suffering from atrial fibrillation or not, said method comprising the steps of
    a) obtaining a plasma or serum sample from the subject;
    b) determining an amount of a BNP-type peptide in the sample of said subject;
    c) comparing the amount of the BNP-type peptide to a reference,
    d) assessing a presence or absence of atrial fibrillation in intermittent electrocardiogram (ECG) recordings obtained from said subject over a period of at least one week by using a handheld ECG device; and
    e) diagnosing whether the subject suffers from atrial fibrillation or not, based on results of steps (c) and (d):
    wherein the absence of atrial fibrillation in the intermittent ECG recordings and an amount of the BNP-type peptide below the reference is indicative for a subject who does not suffer from atrial fibrillation; and wherein the presence of atrial fibrillation in the intermittent ECG recordings and/or an amount of the BNP-type peptide above the reference are indicative for a subject who suffers from atrial fibrillation.

2. The method of claim 1, wherein the BNP-type peptide is NT-proBNP or BNP.

3. The method of claim 1, wherein the handheld ECG device is a one-lead device.

4. The method of claim 3, wherein the handheld ECG device comprises two dry-contact electrodes.

5. The method of claim 4, wherein the intermittent ECG recordings are obtained by placing thumbs on the dry-contact electrodes.

6. The method of claim 1, wherein the handheld ECG device is operated by the subject to be tested.

7. The method of claim 1, wherein the intermittent ECG recordings are obtained at least once daily.

8. The method of claim 1, wherein the intermittent ECG recordings are obtained when the subject shows symptoms of atrial fibrillation.

9. The method of claim 1, wherein the subject is 70 years of age or older.

10. The method of claim 1, wherein the reference for the BNP-type peptide is an age-, gender- and/or weight-specific reference.

11. The method of claim 1, wherein therapy with an anticoagulant is initiated when the subject suffers from atrial fibrillation.

12. The method of claim 1 wherein the sample is a plasma sample that is obtained by collecting whole blood from the subject in anticoagulant-treated tubes, centrifuging the sample, and obtaining a supernatant.

13. The method of claim 1 wherein the sample is serum that is obtained by collecting whole blood from the subject, allowing the whole blood to clot, and obtaining a liquid fraction.

14. The method of claim 1 wherein the ECG recording are sent electronically to a database.

* * * * *